United States Patent
Hara et al.

(10) Patent No.: US 11,767,411 B2
(45) Date of Patent: Sep. 26, 2023

(54) CURABLE COMPOSITION CONTAINING TRANSITION METAL ADSORBENT

(71) Applicant: SHOFU INC., Kyoto (JP)

(72) Inventors: Daisuke Hara, Kyoto (JP); Kenzo Yamamoto, Kyoto (JP); Yasuhiro Nishino, Kyoto (JP); Kazuya Shinno, Kyoto (JP)

(73) Assignee: SHOFU INC., Kyoto (JP)

( * ) Notice: Subject to any disclaimer, the term of this patent is extended or adjusted under 35 U.S.C. 154(b) by 323 days.

(21) Appl. No.: 17/032,284

(22) Filed: Sep. 25, 2020

(65) Prior Publication Data
US 2021/0189098 A1 Jun. 24, 2021

(30) Foreign Application Priority Data
Sep. 26, 2019 (JP) .................. 2019-175382

(51) Int. Cl.
| | |
|---|---|
| C08F 2/46 | (2006.01) |
| C08F 2/50 | (2006.01) |
| C08G 61/04 | (2006.01) |
| C08K 5/00 | (2006.01) |
| C08K 3/11 | (2018.01) |
| C08F 220/12 | (2006.01) |
| C08K 3/16 | (2006.01) |
| C08K 3/22 | (2006.01) |
| C08K 3/30 | (2006.01) |
| C08K 3/36 | (2006.01) |
| C08K 3/40 | (2006.01) |
| C08K 5/1575 | (2006.01) |
| C08K 9/02 | (2006.01) |
| C08K 9/06 | (2006.01) |
| C08L 33/12 | (2006.01) |

(52) U.S. Cl.
CPC .......... C08K 5/0091 (2013.01); C08F 220/12 (2013.01); C08K 3/11 (2018.01); C08K 3/16 (2013.01); C08K 3/22 (2013.01); C08K 3/30 (2013.01); C08K 3/36 (2013.01); C08K 3/40 (2013.01); C08K 5/1575 (2013.01); C08K 9/02 (2013.01); C08K 9/06 (2013.01); C08L 33/12 (2013.01); C08K 2003/2227 (2013.01); C08K 2003/2244 (2013.01); C08K 2003/3045 (2013.01)

(58) Field of Classification Search
CPC ...... C08K 5/0091; C08K 5/1575; C08K 3/16; C08K 3/40; C08K 3/36; C08K 3/11; C08K 3/22; C08K 3/30; C08K 9/02; C08K 9/06; C08K 2003/2244; C08K 2003/2227; C08K 2003/3045; A61K 6/15; A61K 6/30; A61K 6/887; A61K 6/61; A61K 6/60; A61K 6/71; C08F 220/02; C08L 33/12; C08L 33/10
USPC ...... 522/18, 12, 7, 6, 189, 184, 71, 1; 520/1
See application file for complete search history.

(56) References Cited

U.S. PATENT DOCUMENTS

| | | |
|---|---|---|
| 2012/0059083 A1 | 3/2012 | Tokui et al. |
| 2016/0051450 A1 | 2/2016 | Kashiki et al. |

FOREIGN PATENT DOCUMENTS

| | | | |
|---|---|---|---|
| GB | 2075035 | 11/1981 | |
| JP | 2009-292761 | 12/2009 | |
| JP | 2012-51856 | 3/2012 | |
| JP | 2016-098202 | * 11/2014 | |
| WO | WO-2005079607 A1 | * 9/2005 | ........... A23L 3/3436 |

OTHER PUBLICATIONS

Tsuji et al, WO 2005-079607 Machine Translation, Sep. 1, 2005 (Year: 2005).*
Suzuki, JP 2016098202 Machine Translation, Nov. 21, 2014 (Year: 2014).*
Extended European SearchReport issued Mar. 22, 2021 in corresponding European Patent Application No. 20197790.7.
Sagawa et al., "Effect of Annealing on the Visible Photoluminescence Characteristics of Octadecyltrichlorosilane Monolayers on Silica Surfaces", 2008, J. Phys. Chem. C, vol. 112, No. 12, pp. 4581-4589.

* cited by examiner

Primary Examiner — Jessica Whiteley
(74) Attorney, Agent, or Firm — Wenderoth, Lind & Ponack, L.L.P.

(57) ABSTRACT

To provide a dental curable composition having excellent curability and storage stability. The dental curable composition contains (a) transition metal adsorbent in which a transition metal compound of the period 4 in the periodic table is adsorbed on an inorganic particle which is non-reactive with a transition metal of the period 4 in the periodic table, (b) thiourea derivative, (c) organic peroxide having a hydroperoxide group, and (d) polymerizable monomer, wherein the (d) polymerizable monomer contains (d-1) acidic group-non-containing polymerizable monomer, and wherein a pore volume of the inorganic particle which is non-reactive with a transition metal of the period 4 in the periodic table is 0.2 cc/g or less.

16 Claims, No Drawings

US 11,767,411 B2

CURABLE COMPOSITION CONTAINING TRANSITION METAL ADSORBENT

CROSS-REFERENCE TO RELATED APPLICATIONS

This application is based on and claims the benefit of priority from Japanese Patent Application Serial No. 2019-175382 (filed on Sep. 26, 2019), the contents of which are hereby incorporated by reference in their entirety.

BACKGROUND OF THE INVENTION

Field of the Invention

The present disclosure relates to a dental curable composition having excellent storage stability.

Description of the Related Art

In the dental field, a curable composition containing a polymerization initiator consisting of an organic peroxide and their reducing agent and a polymerizable monomer has been widely used as a dental cement, a dental adhesive material, a dental autopolymerizing resin, a dental pretreatment material, and a dental abutment building material and the like.

Paste-like multi-part type curable compositions using an oxidation-reduction reaction of an organic peroxide and a reducing agent thereof as a polymerization initiation reaction have been publicly known, and among them, a multi-part type curable composition using a benzoyl peroxide as an organic peroxide and an aromatic amine as a reducing agent thereof has especially high curability and has been used wider. However, when storing under conditions of high environmental temperature, there is a problem that the storage stability is low and the color changes to yellow or brown occur. As a solution to this problem, a multi-part type curable composition using a hydroperoxide which is an organic peroxide and a thiourea derivative which is a reducing agent thereof is disclosed (Prior Document 1). Although the storage stability and the color tone stability of these multi-part type curable compositions are improved as compared with conventional compositions using a polymerization initiator, the curability is insufficient.

Further, as a technique for overcoming the above problems, a multi-part type curable composition containing a transition metal compound of the period 4 in the periodic table such as a copper compound and a vanadium compound as a polymerization accelerator, in addition to hydroperoxide which is an organic peroxide and a thiourea derivative which is a reducing agent thereof is presented (Prior Document 2). Although the curability of these multi-part type curable compositions is dramatically improved, there is a problem that the storage stability is insufficient.

RELEVANT REFERENCES

Patent Literature

[Patent Document 1]
Japanese Unexamined Patent Application Publication No. 2009-292761
[Patent Document 2]
Japanese Unexamined Patent Application Publication No. 2012-051856

SUMMARY OF THE INVENTION

Technical Problem

Although the compounding of the above transition metal compound of the period 4 in the periodic table is effective for the polymerization reaction, there is a problem that the curability is lowered and the stability after preparation is low.

Solution to Problem

As a result of intensive studies to solve the above problems, a dental curable composition having excellent curability and storage stability has been found by adopting a transition metal adsorbent in which a transition metal compound of the period 4 in the periodic table is adsorbed in advance on a non-reactive inorganic particle, leading to completion of the present invention.

The present disclosure provides a dental curable composition, containing (a) transition metal adsorbent in which a transition metal compound of the period 4 in the periodic table is adsorbed on an inorganic particle which is non-reactive with a transition metal of the period 4 in the periodic table, (b) thiourea derivative, (c) organic peroxide having a hydroperoxide group, and (d) polymerizable monomer, wherein the (d) polymerizable monomer contains (d-1) acidic group-non-containing polymerizable monomer, and wherein a pore volume of the inorganic particle which is non-reactive with a transition metal of the period 4 in the periodic table is 0.2 cc/g or less.

In the dental curable composition of the present disclosure, it is preferable that the (d) polymerizable monomer further contains (d-2) acidic group-containing polymerizable monomer.

In the dental curable composition of the present disclosure, it is preferable that the dental curable composition contains 1 to 40 parts by weight of the (d-2) acidic group-containing polymerizable monomer based on 100 parts by weight of the (d) polymerizable monomer.

In the dental curable composition of the present disclosure, it is preferable that a first paste contains the (a) transition metal adsorbent in which a transition metal compound of the period 4 in the periodic table is adsorbed on an inorganic particle which is non-reactive with a transition metal of the period 4 in the periodic table, the (b) thiourea derivative and the (d) polymerizable monomer, and a second paste contains the (c) organic peroxide having a hydroperoxide group the (d) polymerizable monomer.

In the dental curable composition of the present disclosure, it is preferable that an amount of the transition metal compound of the 4th period adsorbed in the (a) transition metal adsorbent in which a transition metal compound of the period 4 in the periodic table is adsorbed on an inorganic particle which is non-reactive with a transition metal of the period 4 in the periodic table is 0.001 to 0.1 g/m$^2$.

In the dental curable composition of the present disclosure, it is preferable that the dental curable composition contains, based on 100 parts by weight of the total amount of the polymerizable monomer, 0.05 to 7.5 parts by weight of the (a) transition metal adsorbent in which a transition metal compound of the period 4 in the periodic table is adsorbed on an inorganic particle which is non-reactive with a transition metal of the period 4 in the periodic table, 0.001 to 1 parts by weight of transition metal compound contained in the (a) transition metal adsorbent in which a transition metal compound of the period 4 in the periodic table is adsorbed on an inorganic particle which is non-reactive with a transition metal of the period 4 in the periodic table, 0.1 to 4 parts by weight of the (b) thiourea derivative, and 0.1 to 3 parts by weight of the (c) organic peroxide having a hydroperoxide group.

In the dental curable composition of the present disclosure, it is preferable that the dental curable composition further contains, based on 100 parts by weight of the total amount of the polymerizable monomer, 0.5 to 350 parts by weight of a filler, 0.01 to 5 parts by weight of a photopolymerization initiator, and 0.01 to 5 parts by weight of a polymerization accelerator.

Advantageous Effects of Invention

According to the present disclosure, it is possible to provide a dental curable composition having excellent curability and storage stability by adopting a transition metal adsorbent in which a transition metal compound of the period 4 in the periodic table is adsorbed in advance on non-reactive inorganic particles.

DETAILED DESCRIPTION OF THE PREFERRED EMBODIMENTS

The present disclosure will be described in detail below. The (a) transition metal adsorbent in which a transition metal compound of the period 4 in the periodic table is adsorbed on an inorganic particle which is non-reactive with a transition metal of the period 4 in the periodic table of the present disclosure will be described.

The transition metal compound of the period 4 in the periodic table refers to a metal compound of groups 3 to 12 of the period 4 in the periodic table, and specifically, each metal compounds of scandium (Sc), titanium (Ti), vanadium (V), manganese (Mn), iron (Fe), cobalt (Co), nickel (Ni), copper (Cu), and zinc (Zn) can be used without any limitation. Although each of the above transition metal elements may have a multiple valences, they can be added to the curable composition of the present disclosure as long as the valence is stable. Examples include Sc (trivalent), Ti (tetravalent), V (trivalent, tetravalent or pentavalent), Cr (divalent, trivalent or hexavalent), Mn (divalent to heptavalent), Fe (divalent or trivalent), Co (divalent or trivalent), Ni (divalent), Cu (monovalent or divalent), Zn (divalent). Specific examples of the transition metal compound include scandium iodide (trivalent) and the like as a scandium compound, titanium chloride (tetravalent), titanium tetraisopropoxide (tetravalent) and the like as titanium compounds, acetylacetone vanadium (trivalent), divanadium tetraoxide (tetravalent), vanadylacetyl acetonate (tetravalent), vanadium stearate oxide (tetravalent), vanadyl oxalate (tetravalent), vanazyl sulfate (tetravalent), oxobis (1-phenyl-1,3-butandionate) vanadium (tetravalent), bis (maltlate) oxovanadium (tetravalent), vanadium pentoxide (pentavalent), sodium metavanadate (pentavalent) and the like as a vanadium compound, manganese acetate (divalent), manganese naphthenate (divalent) and the like as manganese compounds, iron acetate (divalent), iron chloride (divalent), iron acetate (trivalent), iron chloride (trivalent) and the like as an iron compound, cobalt acetate (divalent), cobalt naphthenate (divalent) and the like as a cobalt compound, nickel chloride (divalent) and the like as a nickel compound, copper chloride (monovalent), copper bromide (monovalent), copper chloride (divalent), copper acetate (divalent) and the like as a copper compound, and zinc chloride (divalent), zinc acetate (divalent) and the like as a zinc compound.

Among these, a trivalent or tetravalent vanadium compound and a divalent copper compound are preferable. Among them, because of having higher polymerization accelerating ability, a trivalent or tetravalent vanadium compound is more preferable, and a tetravalent vanadium compound is most preferable. A plurality of kinds of these transition metal compounds in the period 4 in the periodic table may be used in combination, if necessary. The content of the transition metal compound to be compounded is preferably within a range of 0.001 to 1 parts by weight, more preferably within a range of 0.005 to 0.5 parts by weight, based on 100 parts by weight of the total amount of all polymerizable monomers. When the content is less than 0.001 parts by weight, there is a case where the polymerization accelerating effect is insufficient, and when the content exceeds 1 parts by weight, there is a case where it causes discoloration or gelation of the curable composition, and the storage stability is lowered.

As the inorganic particle which is non-reactive with a transition metal of the period 4 in the periodic table (hereinafter, also simply referred as "non-reactive inorganic particle" in the present specification), any inorganic particle can be preferably used as long as the inorganic particle not only does not react with the transition metal compound of the period 4 in the periodic table (hereinafter, also simply referred as "transition metal compound" in the present specification), but also does not interact with an oxidation-reduction reaction of an organic peroxide and a reducing agent thereof. As the non-reactive inorganic particle, oxides such as silica, zirconia, calcium, titania and alumina, composite oxides (glass) thereof, metal fluorides such as trifluoroitterbium and sodium fluoride, sulfates such as magnesium sulfate and barium sulfate can be used. Among these, composite oxides, metal fluorides and sulfates are preferable, and especially trifluoro ytterbium and barium sulfate are more preferable. A plurality of kinds of these non-reactive inorganic particles may be used in combination, if necessary. The primary particle diameter of the non-reactive inorganic particles is preferably within a range of 0.01 to 50 μm, more preferably within a range of 0.01 to 20 μm from the viewpoint of dispersibility. When the primary particle diameter of the non-reactive inorganic particles is less than 0.01 μm, there is a case where the cohesiveness becomes high and the dispersibility into the polymerizable monomer is lowered, and when the primary particle diameter of the non-reactive inorganic particles is more than 50 μm, there is a case where the non-reactive inorganic particles are non-uniformly dispersed in the composition and it is difficult to sufficiently accelerate the polymerization.

Further, as for the shape, any non-porous particle can be used without any limitation, and examples thereof include a spherical shape, a crushed shape, and an indefinite shape. In a case of a porous particle, an opportunity to react the transition metal compound adsorbed in the pores as a polymerization accelerator reduces, therefore the polymerization accelerating efficiency may be lowered and an unreacted residue may be prepared to cause discoloration. Therefore, the pore volume of the non-reactive inorganic particle in the present disclosure is 0.2 cc/g or less, preferably 0.15 cc/g or less, and most preferably 0.1 cc/g or less. The pore volume, for example, can be determined by the BJH method, and the pore volume is that of the aggregated particle when the non-reactive inorganic particle is an aggregated particle.

As for a method for adsorbing a transition metal compound to a non-reactive inorganic particle, both a physical adsorption method and a chemical adsorption method can be used without any limitation. Specifically, chemical adsorption methods such as a hydrophobic adsorption, a deposition-precipitation method, an impregnation method, a coprecipitation method, an ion exchange method and an equilibrium adsorption method and physical adsorption methods can be used, but physical adsorption method is preferable from the viewpoint of production efficiency. More specifically, a method of obtaining a transition metal adsorbent adsorbing a transition metal compound by dissolving or dispersing in an organic solvent having a high affinity with the transition metal compound and having a low boiling point, and removing the organic solvent after mixing with non-reactive inorganic particles, and a method of depositing a transition metal particle on the surface of an inorganic particle by adding a poor solvent after dissolving in a good solvent having a high affinity with a transition metal compound, and a method of physically adsorbing a transition metal compound on the inorganic particle surface by using a pot mill, a ball mill, a planetary mill and the like are preferable.

The adsorption amount of the transition metal compound on the non-reactive inorganic particle is preferably within a range of 0.001 to 0.1 $g/m^2$, more preferably within a range of 0.001 to 0.05 $g/m^2$ in terms of the adsorption amount per unit area of the inorganic particle. When the amount is less than 0.001 $g/m^2$, there is a case where the polymerization accelerating effect is insufficient, and when the amount is more than 0.1 $g/m^2$ or more, there is a case where the polymerization accelerating effect is excessive, and therefore discoloration and the like occurs and the storage stability is lowered. In the present disclosure, when a plurality of the (a) transition metal adsorbent in which a transition metal compound of the period 4 in the periodic table is adsorbed on an inorganic particle which is non-reactive with a transition metal of the period 4 in the periodic table are contained, it is preferable that the adsorption amount of any one of the (a) transition metal adsorbent in which a transition metal compound of the period 4 in the periodic table is adsorbed on an inorganic particle which is non-reactive with a transition metal of the period 4 in the periodic table is within the above range, and it is more preferable that the adsorption amounts in all (a) transition metal adsorbent in which a transition metal compound of the period 4 in the periodic table is adsorbed on an inorganic particle which is non-reactive with a transition metal of the period 4 in the periodic table are within the above range.

The content of the (a) transition metal adsorbent in which a transition metal compound of the period 4 in the periodic table is adsorbed on an inorganic particle which is non-reactive with a transition metal of the period 4 in the periodic table to be compounded is preferably within a range of 0.05 to 7.5 parts by weight, more preferably within a range of 0.05 to 5 parts by weight, based on 100 parts by weight of the total amount of the polymerizable monomer. When the content is less than 0.05 parts by weight, there is a case where the ability as a polymerization accelerator is insufficient, and when the content exceeds 7.5 parts by weight, the discoloring may be caused by localization.

Any known thiourea derivatives can be used as the (b) thiourea derivative of the present disclosure without any limitation. Specific examples of the thiourea derivatives include dimethylthiourea, diethylthiourea, tetramethylthiourea, (2-pyridyl) thiourea, N-methylthiourea, ethylenethiourea, N-allylthiourea, N-allyl-N'-(2-hydroxyethyl) thiourea, N-benzylthiourea, 1,3-dicyclohexyl thiourea, N,N'-diphenylthiourea, 1,3-di(p-tolyl) thiourea, 1-methyl-3-phenylthiourea, N-acetylthiourea, N-benzoylthiourea, diphenylthiourea, dicyclohexylthiourea and the like. Among these, N-acetylthiourea and N-benzoylthiourea are preferable. A plurality of kinds of these thiourea derivatives can be used in combination, if necessary. The content of the thiourea derivative to be compounded is preferably within a range of 0.1 to 4 parts by weight based on 100 parts by weight of the total amount of all polymerizable monomers. When the content is less than 0.1 parts by weight, there is a case where the ability as a polymerization accelerator is insufficient, and when the content exceeds 4 parts by weight, the storage stability may be lowered.

Any known organic peroxides having a hydroperoxide group can be used as the (c) organic peroxide having a hydroperoxide group of the present disclosure without any limitation. Specific examples of the organic peroxides include t-butyl hydroperoxide, cyclohexyl hydroperoxide, cumene hydroperoxide, diisopropylbenzene hydroperoxide, p-menthane hydroperoxide, diisopropylbenzene hydroperoxide, 1,1,3,3-tetramethylbutyl hydroperoxide and the like, and cumene hydroperoxide is preferable from the view point of reactivity. A plurality of kinds of these organic peroxides can be used in combination, if necessary. The content of the organic peroxide having a hydroperoxide group to be compounded is preferably within a range of 0.1 to 3 parts by weight based on 100 parts by weight of the total amount of all polymerizable monomers. When the content is less than 0.1 parts by weight, there is a case where the ability as a polymerization accelerator is insufficient, and when the content exceeds 3 parts by weight, the storage stability may be lowered.

The (d) polymerizable monomer of the present disclosure contains the (d-1) acidic group-non-containing polymerizable monomer. It is preferable that the (d) polymerizable monomer contains the (d-2) acidic group-containing polymerizable monomer. The (d) polymerizable monomer may consists of the (d-1) acidic group-non-containing polymerizable monomer.

Any known polymerizable monomer having one or more polymerizable groups can be used as the (d-1) acidic group-non-containing polymerizable monomer without any limitation. A polymerizable monomer in which the polymerizable group exhibits radical polymerizability is preferable. Specifically, from the viewpoint of easy radical polymerization, (meth)acryl group and/or (meth)acrylamide group is preferable as the polymerizable group. In the present specification, "(meth)acryl" means acryl and/or methacryl, "(meth)acryloyl" means acryloyl and/or methacryloyl, and, "(meth)acrylate" means acrylate and/or methacrylate.

Specific examples of a polymerizable monomer having one radical polymerizable group and not containing acidic group include 2-hydroxyethyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono (meth)acrylate, glycerol mono (meth)acrylate, erythritol mono (meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, butyl (meth)acrylate, isobutyl (meth) crylate, benzyl (meth)acrylate, lauryl (meth)acrylate, 2,3-dibromopropyl (meth)acrylate, 3-(meth)acryloyloxypropyl trimethoxysilane, 11-(meth)acryloyloxyundecyl trimethoxysilane, (meth)acrylamide and the like. Among these, from the viewpoint of high affinity of the curable composition to be obtained with the tooth substance, 2-hydroxyethyl (meth) acrylate, 3-hydroxypropyl (meth)acrylate, glycerol mono (meth)acrylate and erythritol mono (meth)acrylate are preferable.

Specific Examples of the polymerizable monomer having two radical polymerizable groups and not containing acidic group include 2,2-bis ((meth)acryloyloxy phenyl) propane, 2,2-bis [4-(3-(meth)acryloyloxy)-2-hydroxy propoxyphenyl] propane (generally called "Bis-GMA"), 2,2-bis (4-(meth)acryloyloxy phenyl) propane, 2,2-bis (4-(meth)acryloyloxy polyethoxyphenyl) propane, 2,2-bis (4-(meth) acryloyloxy diethoxyphenyl) propane), 2,2-bis (4-(meth) acryloyloxy tetraethoxyphenyl) propane, 2,2-bis (4-(meth) acryloyloxy pentaethoxyphenyl) propane, 2,2-bis (4-(meth) acryloyloxy dipropoxypheny) propane, 2-(4-(meth) acryloyloxy diethoxyphenyl)-2-(4-(meth)acryloyloxy diethoxyphenyl) propane, 2-(4-(meth)acryloyloxy diethoxyphenyl)-2-(4-(meth)acryloyloxy triethoxyphenyl) propane, 2-(4-(meth)acryloyloxy dipropoxyphenyl)-2-(4-(meth)acryloyloxy triethoxyphenyl) propane, 2,2-bis (4-(meth)acryloyloxy propoxyphenyl) propane, 2,2-bis (4-(meth)acryloyloxy isopropoxyphenyl) propane, 1,4-bis (2-(meth)acryloyloxyethyl) pyromellitate, glycerol di(meth)acrylate, ethyleneglycol di(meth)acrylate, diethyleneglycol di(meth)acrylate, triethylene glycol di(meth)acrylate, propylene glycol di(meth) acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like. Among these, from the viewpoint of mechanical strength, 2,2-bis ((meth)acryloyloxy phenyl) propane, 2,2-bis[4-(3-(meth)acryloyloxy)-2-hydroxy propoxyphenyl] propane, 2,2,4-trimethyl hexamethylene bis (2-carbamoyloxyethyl) dimethacrylate and 2,2-bis(4-(meth) acryloyloxy polyethoxyphenyl) propane are preferable, and from the viewpoint of handleability, triethyleneglycol di(meth)acrylate, neopentylglycol di(meth)acrylate and glycerol di(meth)acrylate are preferable. Among the 2,2-bis (4-(meth)acryloyloxy polyethoxyphenyl) propanes, a compound having an average addition mole number of ethoxy group of 2.6 (generally called "D2.6E") is preferable.

Specific Examples of the polymerizable monomer having three or more radical polymerizable groups and not containing acidic group include trimethylolpropane tri(meth)acrylate, trimethylolethane tri(meth)acrylate, trimethylolethane tri(meth)acrylate, pentaerythritol tri(meth)acrylate, pentaerythritol tetra(meth)acrylate, dipentaerythritol penta(meth)acrylate, N,N-(2,2,4-trimethyl hexamethylene) bis [2-(aminocarboxy) propane-1,3-diol] tetramethacrylate, 1,7-diacryloyloxy-2,2,6,6-tetraacryloyl oxymethyl-4-oxyheptane and the like. Among these, trimethylolpropane tri(meth)acrylate is preferable in that the mechanical strength of the resulting curable composition is large.

A plurality of kinds of these (d-1) acidic group-noncontaining polymerizable monomers may be used in combination, if necessary. From the viewpoint of improving mechanical properties, the content of the polymerizable monomer having two radical polymerizable groups and not containing acidic group to be compounded is preferably set to within a range of 40 to 100 parts by weight, more preferably within a range of 60 to 90 parts by weight based on 100 parts by weight of the total amount of all polymerizable monomers in the curable composition. When the content of the polymerizable monomer having two radical polymerizable groups and not containing acidic group is less than 40 parts by weight, there is a case in which mechanical properties may be lowered.

The curable composition of the present disclosure may be compounded with the (d-2) acidic group-containing polymerizable monomer in order to impart adhesive property to a tooth substance and a prosthetic device attached in an oral cavity. Any polymerizable monomer having one or more polymerizable groups and having at least one acidic group such as a phosphoric acid group, a pyrophosphate group, a thiophosphate group, a phosphonic acid group, a sulfonic acid group, a carboxylic acid group as acid groups can be used as the (d-2) acidic group-containing polymerizable monomer without any limitation.

Specific examples of an acidic group-containing polymerizable monomer which has a phosphoric acid group are not limited to, but include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis [2-(meth)acryloyl oxyethyl] hydrogensphosphate, bis [4-(meth)acryloyl oxybutyl] hydrogen phosphate, bis [6-(meta)acryloyl oxyhexyl] hydrogen phosphate, bis [8-(meth)acryloyl oxyoctyl] hydrogen phosphate, bis [9-(meth) acryloyl oxynonyl] hydrogen phosphate, bis [10-(meth) acryloyl oxydecyl] hydrogen phosphate, 1,3-di(meth) acryloyl oxypropyl dihydrogenphosphate, 2-(meth)acryloyl oxyethylphenyl hydrogen phosphate, 2-(meth)acryloyloxyethyl-2-bromoethyl hydrogen phosphate and bis [2-(meth) acryloyloxy-(1-hyrdoxymethyl) ethyl] hydrogen phosphate; acyl chloride, alkali metal salt and ammonium salt thereof; and (meth)acrylamide compound in which the ester bond of these compounds is replaced with an amide bond, and the like.

Specific examples of an acidic group-containing polymerizable monomer which has a pyrophosphoryl group are not limited to, but include, bis [2-(meth)acryloyl oxyethyl] pyrophosphate, bis [4-(meth)acryloyl oxybutyl] pyrophosphate, bis [6-(meth)acryloyl oxyhexyl] pyrophosphate, bis [8-(meth)acryloyl oxyoctyl] pyrophosphate, bis [10-(meth) acryloyl oxydecyl] pyrophosphate; acyl chloride, alkali metal salt and ammonium salt thereof; and (meth)acrylamide compound in which the ester bond of these compounds is replaced with an amide bond, and the like.

Specific examples of an acidic group-containing polymerizable monomer which has a thiophosphoryl group are not limited to, but include, 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyeicocyl dihydrogen thiophosphate; acyl chloride, alkali metal salt and ammonium salt thereof; and (meth)acrylamide compound in which the ester bond of these compounds is replaced with an amide bond, and the like.

Specific examples of an acidic group-containing polymerizable monomer which has a phosphonic acid group are not limited to, but include, 2-(meth)acryloyloxy ethylphenyl phosphonate, 5-(meth)acryloyloxy pentyl-3-phosphonopropionate, 6-(meth)acryloyloxy hexyl-3-phosphonopropionate, 10-(meth)acryloyloxy decyl-3-phosphonopropionate, 6-(meth)acryloyloxy hexyl-3-phosphonoacetate, 10-(meth)acryloyloxy decyl-3-phosphonoacetate; acyl chloride, alkali metal salt and ammonium salt thereof; and (meth)acrylamide compound in which the ester bond of these compounds is replaced with an amide bond, and the like.

Specific examples of an acidic group-containing polymerizable monomer which has sulfonic acid group are not limited to, but include, 2-(meth)acrylamide-2-methyl propane sulfonic acid and 2-sulfoethyl (meth)acrylate and the like.

Examples of an acidic group-containing polymerizable monomer which has a carboxylic acid group include a (meth)acrylic-based compound having one carboxyl group in the molecule and a (meth)acrylic-based compound having a plurality of carboxyl groups in the molecule. Specific examples of the (meth)acrylic-based compound having one carboxyl group in the molecule include (meth)acrylic acid, N-(meth)acryloylglycine, N-(meth)acryloyl asp artic acid, o-(meth)acryloyl tyrosine, N-(meta)acryloyl tyrosine, N-(meth)acryloyl phenylalanine, N-(meth)acryloyl-p-amino benzoic acid, N-(meth)acryloyl-o-amino benzoic acid, p-vinyl benzoic acid, 2-(meta)acryloyloxy benzoic acid, 3-(meth)acryloyloxy benzoic acid, 4-(meth)acryloyloxy benzoic acid, N-(meth)acryloyl-5-amino salicylic acid, N-(meth)acryloyl-4-amino salicylic acid, 2-(meta)acryloyloxyethyl hydrogen succinate, 2-(meth)acryloyloxyethyl hydrogen phthalate, 2-(meth)acryloyloxyethyl hydrogen malate; acid halides thereof; and (meth)acrylamide compound in which the ester bond of these compounds is replaced with an amide bond, and the like. Examples of the (meth)acrylic-based compound having a plurality of carboxyl groups in the molecule include 6-(meth)acryloyl oxyhexane-1,1-dicarboxylic acid, 9-(meth)acryloyl oxynonane-1,1-dicarboxylic acid, 10-(meth)acryloyl oxydecane-1,1-dicarboxylic acid, 11-(meth)acryloyloxy undecane-1,1-dicarboxylic acid, 12-(meth)acryloyl oxydodecane-1,1-dicarboxylic acid, 13-(meta)acryloyloxy tridecane-1,1-dicarboxylic acid, 4-(meth)acryloyl oxyethyl trimerite, 4-(meth)acryloyl oxybutyl trimerite, 4-(meth)acryloyl oxyhexyl trimerite, 4-(meta)acryloyl oxydecyl trimerite, 2-(meth)acryloyl oxyethyl-3'-(meth)acryloyloxy-2'-(3,4-dicarboxy benzoyloxy) propylsuccinate; acid anhydrides and acid halides thereof; and (meth)acrylamide compound in which the ester bond of these compounds is replaced with an amide bond, and the like.

Among the above-described acidic group-containing polymerizable monomers, it is preferable to have a phosphoric acid group or a phosphonic acid group from the view point of the adhesive property of the dental curable composition. Especially, it is preferable to have an alkyl group or an alkylene group having 4 or more the carbon number of a main chain in the molecule, and 10-(meth)acryloyl oxydecyl dihydrogen phosphate and (6-methacryloyloxy) hexylphosphonoacetate are more preferable. A plurality of kinds of these acidic group-containing polymerizable monomers can be used in combination, if necessary. Further, the content of the acidic group-containing polymerizable monomer to be compounded is preferably within a range of 1 to 40 parts by weight more preferably within a range of 2 to 20 parts by weight, based on 100 parts by weight of the total amount of all polymerizable monomers from the viewpoint of the adhesive property.

Any known fillers can be compounded in the curable composition of the present disclosure according to its use without any limitation. For example, when it is used as a dental adhesive material such as a dental direct restoration adhesive material (bonding material) or a dental indirect restoration adhesive material, and a dental restoration material as a dental prosthesis such as a composite resin, it is preferable to compound a filler such as an inorganic filler, an organic filler and an organic-inorganic composite filler. It is preferable that the filler is silane treated. By silane treatment, a large amount can be filled in the composition. As the silane treatment agent, an ordinary silane treatment agent can be used.

Examples of the above-described inorganic filler include quartz, silica, silica-alumina, silica-titania, silica-zirconia, silica-magnesia, silica-calcia, silica-valium oxide, silica-strontium oxide, silica-titania-sodium oxide, silica-titania-potassium oxide, titania, zirconia, alumina, glass filler and the like. More specific glass fillers include silicate glass, fluoroaluminosilicate glass, fluoroboroaluminosilicate glass, barium glass and the like. If necessary, these inorganic fillers may be surface-treated with a silane coupling agent such as γ-methacryloxypropyl trimethoxysilane, ε-methacryloxyoctyl trimethoxysilane and vinyltrimethoxysilane.

Examples of the organic filler include polymers such as polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinylchloride, polystyrene, chlorinated polyethylene, nylon, polysulfone, polyethersulfone and polycarbonate.

Examples of the organic-inorganic composite filler include pulverized composites of the above-mentioned inorganic oxide (inorganic filler) and polymer (organic filler).

The particle shape of the above described various fillers is not particularly limited, and may be a pulverized particles obtained by usual pulverization or a spherical particles. Further, the particle diameter of these fillers is not particularly limited, but generally from the viewpoint of the dispersibility and the like, is preferably 100 µm or less, particularly preferably 30 µm or less. The content of the filler to be compounded is preferably within a range of 0.5 to 350 parts by weight, more preferably within a range of 1 to 300 parts by weight based on 100 parts by weight of the total amount of all polymerizable monomers.

A photopolymerization initiator may be compounded in the curable composition of the present disclosure in order to impart photopolymerizability. Specific examples of the photopolymerization initiator include α-diketones, mono-, bis-, or tris acylphosphine oxide compound and mono- or diacylgermanium compound. The content of the photopolymerization initiator to be compounded is not particularly limited, however from the viewpoint of photocurability, is preferably within a range of 0.01 to 5 parts by weight, more preferably within a range of 0.1 to 3 parts by weight based on 100 parts by weight of the total amount of all polymerizable monomers.

Specific examples of α-diketones include diacetyl, dibenzyl, camphor quinone, 2,3-pentadione, 2,3-octadione, 9,10-phenanthrenequinone, 4,4'-oxybenzyl, acenaphthenequinone and the like. Among these, camphor quinone is preferable because it is excellent in photocurability in the visible and near-ultraviolet regions and exhibits sufficient photocurability even if any light source of a halogen lamp, a light emitting diode (LED) and a xenon lamp are used.

Examples of mono-, bis-, or tris acylphosphine oxide compound include bis (2,6-dimethoxy benzoyl) phenyl phosphine oxide, bis (2,6-dimethoxy benzoyl) (2,4,4-trimethyl pentyl) phosphine oxide, bis (2,6-dimethoxy benzoyl)-n-butyl phosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxy benzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide, 2,6-dimethoxy benzoyl-2,4,6-trimethyl benzoyl-n-butyl phosphine oxide and the like. Among these, from the viewpoint of photocurability, bis (2,6-dimethoxy benzoyl) (2,4,4-trimethyl pentyl) phosphine oxide and 2,4,6-trimethyl benzoyl diphenyl phosphine oxide are preferable.

Examples of mono- or di-acylgermanium compound include bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium and (4-methoxybenzoyl) diethylgermanium and the like are mentioned.

In the curable composition of the present disclosure, in order to further improve the curability, a polymerization accelerator may further be compounded. Examples polymerization accelerators include an aliphatic amine, an aromatic amine, a sulfinic acid derivative, a sulfur-containing reductive inorganic compound, a nitrogen-containing reductive inorganic compound, a borate compound, a barbituric acid derivative, a triazine compound, a halogen compound and the like. The content of the polymerization accelerator to be compounded is preferably within a range of 0.01 to 5 part by weight, more preferably within a range of 0.1 to 3 parts by weight based on 100 parts by weight of the total amount of all polymerizable monomers.

Specific examples of aliphatic amine include primary aliphatic amines such as n-butylamine, n-hexylamine and n-octylamine; secondary aliphatic amines such as diisopropylamine and dibutylamine; tertiary aliphatic amines such as N-methyl diethanolamine, N-ethyl diethanolamine, N-n-butyl diethanolamine, N-lauryl diethanolamine, 2-(dimethylamino) ethyl (meth)acrylate, N-methyl diethanolamine di(meth)acrylate, N-ethyl diethanolamine di(meth)acrylate, triethanolamine mono (meth)acrylate, triethanolamine di(meth)acrylate, triethanolamine tri(meth)acrylate, triethanolamine, trimethylamine, triethylamine and tributylamine and the like. Among these, tertiary aliphatic amines are preferable from the viewpoint of the curability and storage stability of the composition, and among them, 2-(dimethyl amino) ethyl (meth)acrylate and N-methyl diethanolamine di(meth)acrylate are preferable.

Specific examples of the aromatic amine compound include 2,2-[3-(methylphenyl) imino] bisethanol acetate, 1,1-[(4-methylphenyl) imino] bis (2-propanol), p-tolyldiethanol amine, N,N-bis (2,2,2-trifluoroethyl)-p-toluidine, N,N-di(1-hydroxyethyl)-p-toluidine, N,N-di(2-hydroxypropyl)-p-toluidine, N-(1-cyanoethyl)-N-(1-acetoxyethyl)-m-toluidine, N,N-di(1-chloroethyl)-p-toluidine, N,N-dimethyl-p-toluidine, N-ethyl-N-methylaniline, N,N-dimethylaniline, N,N-dipropyl-o-toluidine, N,N-dipropyl-m-toluidine, N,N-dipropyl-p-toluidine, ethyl 4-dimethylaminobenzoate and the like. Among these aromatic amine compounds, ethyl 4-dimethylaminobenzoate is preferably used because of excellent solubility in polymerizable monomers and high storage stability.

Examples of sulfinic acid derivative include salts (alkali metals or alkaline earth metals are preferred) of p-toluene sulfinic acid, benzene sulfinic acid, 2,4,6-trimethylbenzene sulfinic acid, 2,4,6-triethylbenzene sulfinic acid, 2,4,6-triisopropylbenzene sulfinic acid and the like. Specific examples of salt compounds of these sulfinic acids include sodium p-toluenesulfinate and sodium benzenesulfinate.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite and the like.

Examples of nitrogen-containing reductive inorganic compound include nitrites, and specific examples include sodium nitrite, potassium nitrite, calcium nitrite, ammonium nitrite and the like.

Specific examples of borate compound include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the triazine compound include 2,4,6-tris (trichloro methyl)-s-triazine, 2,4,6-tris (tribromo methyl)-s-triazine, 2-methyl-4,6-bis (trichloro methyl)-s-triazine, 2-methyl-4,6-bis (tribromo methyl)-s-triazine, 2-phenyl-4,6-bis (trichloro methyl)-s-triazine, 2-(p-methoxy phenyl)-4,6-bis (trichloro methyl)-s-triazine, 2-(p-methyl thiophenyl)-4,6-bis (trichloro methyl)-s-triazine, 2-(p-chloro phenyl)-4,6-bis (trichloro methyl)-s-triazine, 2-(2,4-dichloro phenyl)-4,6-bis (trichloro methyl)-s-triazine, 2-(p-bromo phenyl)-4,6-bis (trichloro methyl)-s-triazine, 2-(p-tolyl)-4,6-bis (trichloro methyl)-s-triazine, 2-n-propyl-4,6-bis (trichloro methyl)-s-triazine, 2-($\alpha,\alpha,\beta$-trichloro ethyl)-4,6-bis (trichloro methyl)-s-triazine, 2-styryl-4,6-bis (trichloro methyl)-s-triazine, 2-[2-(p-methoxy phenyl) ethenyl]-4,6-bis (trichloro methyl)-s-triazine, 2-[2-(o-methoxy phenyl) ethenyl]-4,6-bis (trichloro methyl)-s-triazine, 2-[2-(p-butoxy phenyl) ethenyl]-4,6-bis (trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis (2-hydroxy ethyl) amino} ethoxy]-4,6-bis (trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis (trichloro methyl)-s-triazine, 2-[2-{N,N-diallylamino} ethoxy]-4,6-bis (trichloro methyl)-s-triazine and the like.

Specific examples of the halogen compound include dilauryl dimethyl ammoniumchloride, lauryl dimethylbenzyl ammoniumchloride, benzyl trimethyl ammoniumchloride, tetramethyl ammoniumchloride, benzyl dimethylacetyl ammoniumchloride, dilauryl dimethyl ammonium romide and the like.

In the curable composition of the present disclosure, in order to further improve the storage stability, a metal supplementary material may be compounded. The curability of the curable composition of the present disclosure is remarkably changed by contamination with a trace amount of metal element. Metal supplementary material such as an aminocarboxylic acid-based chelating agent and a phosphonic acid-based chelating agent may be compounded in order to minimize the influence on the curability caused by the mixing of a trace amount of metal element in the raw material and the contamination of metal element in a preparing process. Examples of the aminocarboxylic acid-based chelating agent include ethylenediamine tetraacetic acid and sodium salt thereof, nitrilotriacetic acid and a sodium salt thereof, diethylene triamine pentacetic acid and a sodium salt thereof, N-(2-hydroxyethyl) ethylenediamine triacetic acid and a sodium salt thereof, triethylene tetramine N,N,N',N'',N''',N'''-hexacetic acid and a sodium salt thereof, 1,3-propane diamine-N,N,N',N'-tetraacetic acid and a sodium salt thereof, 1,3-diamino-2-propanol-N,N,N',N'-tetraacetic acid and a sodium salt thereof, hydroxyethylimino diacetic acid and a sodium salt thereof, N,N-di(2-hydroxyethyl) glycin and a sodium salt thereof, glycol ether diamine tetraacetic acid and a sodium salt thereof. Examples of the phosphonic acid-based chelating agent include etidronic acid and a sodium salt thereof, nitrile tris (methylenephosphonic acid) and a sodium salt thereof, 2-phosphonobutane-1,2,4-tricarboxylic acid and a sodium salt thereof. Among these, ethylene diamine tetraacetic acid and a sodium salt thereof are preferable from the viewpoint of metal supplementary ability. A plurality of kinds of these metal supplementary materials can be used in combination, if necessary. Further, the content of the metal supplementary material to be compounded is preferably within a range of 1 part by weight or less based on 100 parts by weight of the total amount of polymerizable monomers from the view point of the curability, and when the content exceeds 1 part by weight, the curability of the composition may be lowered.

Moreover, the curable composition of the present disclosure may be compounded with a well-known additives in the range in which as long as the properties does not decrease. Specific examples of such additives include polymerization inhibitors, antioxidants, pigments, dyes, ultraviolet absorbers, organic solvents, thickeners and the like.

The dental curable composition of the present disclosure can be a two-paste type consisting of a first paste and a second paste. In this case, a mixing ratio of the first paste and the second paste is, in terms of a volume ratio, usually 1:7 to 7:1, preferably 1:4 to 4:1, and more preferably 1:2 to 2:1, most preferably 1:1. The mixing ratio of the first paste and the second paste can be set within a range that satisfies a desired ratio for each component.

The dental curable composition of the present disclosure in the case of the two-paste type can be prepared by uniformly mixing each material with a kneading device such as a double planetary mixer or a rotation and revolution mixer.

In the dental curable composition of the present disclosure, a transition metal compound of the period 4 in the periodic table in the (a) transition metal adsorbent, the (b) thiourea derivative and the (c) organic peroxide having a hydroperoxide group are indispensable for the initiation reaction of the polymerization. Although the combination of compounding in the first and second pastes can be appropriately selected, it is preferable that the first paste contains the (a) transition metal adsorbent in which a transition metal compound of the period 4 in the periodic table is adsorbed on an inorganic particle which is non-reactive with a transition metal of the period 4 in the periodic table, the (b) thiourea derivative and the (d) polymerizable monomer and the second paste contains the (c) organic peroxide having a hydroperoxide group, and the (d) polymerizable monomer.

EXAMPLES

Hereinafter, the present invention will be described in detail with reference to Examples and Comparative Examples. However, the present invention is not limited to these Examples. The abbreviations used below are as follows.

[Preparation of Transition Metal Adsorbent]

The preparation method of the transition metal adsorbent in which a transition metal compound of the period 4 in the periodic table is adsorbed on an inorganic particle which is non-reactive with a transition metal of the period 4 in the periodic table is as follows.

(Transition Metal Adsorbent 1)

An eggplant flask was put with 10 g of barium sulfate (BMH-40: manufactured by Sakai Chemical Industry Co., Ltd.) having the average particle diameter of 4.5 μm, the pore volume of 0.06 cc/g and the specific surface area of 5.2 m$^2$/g, and 1 g of vanadyl acetylacetonate (hereinafter, referred as "VOA": manufactured by Tokyo Kasei Kogyo Co., Ltd.) to add the barium sulfate and vanadyl acetylacetonate into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 1 in which 0.0192 g/m$^2$ of a transition metal compound was adsorbed on the surface.
(Transition Metal Adsorbent 2)

A pot was put with 10 g of trifluoro ytterbium (manufactured by Tribach) having the average particle diameter of 0.2 μm, the pore volume of 0.05 cc/g and the specific surface area of 8.1 m$^2$/g, and 1 g of VOA, and was added with 200 g of alumina ball stone having φ2 mm. Then, after treating with a planetary mill (manufactured by Fritsch: P-5 planetary ball mill Classic Line) at 200 rpm for 2 minutes, pass through a #200 mesh were performed to obtain a transition metal adsorbent 2 in which 0.0124 g/m$^2$ of a transition metal compound was adsorbed on the surface.
(Transition Metal Adsorbent 3)

An eggplant flask was put with 10 g of barium sulfate (BMH-10: manufactured by Sakai Chemical Industry Co., Ltd.) having the average particle diameter of 12.0 μm, the pore volume of 0.04 cc/g and the specific surface area of 2.2 m$^2$/g, and 1 g of vanadium oxide stearate (hereinafter, referred as "VOS": manufactured by Tokyo Kasei Kogyo Co., Ltd.) to add the barium sulfate and the vanadium oxide stearate into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 3 in which 0.0454 g/m$^2$ of a transition metal compound was adsorbed on the surface.
(Transition Metal Adsorbent 4)

An eggplant flask putting was put with 10 g of barium sulfate (BF-40: manufactured by Sakai Chemical Industry Co., Ltd.) having the average particle diameter of 0.015 μm, the pore volume of 0.09 cc/g and the specific surface area of 90 m$^2$/g, and 1 g of VOA to add the barium sulfate and the VOA into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 4 in which 0.00111 g/m$^2$ of a transition metal compound was adsorbed on the surface.
(Transition Metal Adsorbent 5)

An eggplant flask putting was put with 10 g of barium sulfate (BMH-40: manufactured by Sakai Chemical Industry Co., Ltd.) having the average particle diameter of 4.5 μm, the pore volume of 0.06 cc/g and the specific surface area of 5.2 m$^2$/g, and 2 g of VOA to add the barium sulfate and the VOA into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 5 in which 0.03846 g/m$^2$ of a transition metal compound was adsorbed on the surface.
(Transition Metal Adsorbent 6)

An eggplant flask putting was put with 50 g of barium sulfate (BMH-40: manufactured by Sakai Chemical Industry Co., Ltd.) having the average particle diameter of 4.5 μm, the pore volume of 0.06 cc/g and the specific surface area of 5.2 m$^2$/g, and 1 g of VOA to add the barium sulfate and the VOA into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 6 in which 0.00385 g/m$^2$ of a transition metal compound was adsorbed on the surface.
(Transition Metal Adsorbent 7)

A pot was put with 10 g of spherical silica particle (SO—C6: manufactured by Admafine Co., Ltd.) having the average particle diameter of 1.4 μm, the pore volume of 0.01 cc/g and the specific surface area of 4.2 m$^2$/g, and 1 g of VOA, and was added with 200 g of alumina ball stone having φ2 mm. Then, after treating with a planetary mill (manufactured by Fritsch: P-5 planetary ball mill Classic Line) at 200 rpm for 2 minutes, pass through a #200 mesh were performed to obtain a transition metal adsorbent 7 in which 0.0238 g/m$^2$ of a transition metal compound was adsorbed on the surface.
(Transition Metal Adsorbent 8)

A pot was put with 10 g of spherical silica particle (SO—C1: manufactured by Admafine Co., Ltd.) having the average particle diameter of 0.3 μm, the pore volume of 0.01 cc/g and the specific surface area of 14.6 m$^2$/g, and 2 g of VOA, and was added with 200 g of alumina ball stone having φ2 mm. Then, after treating with a planetary mill (manufactured by Fritsch: P-5 planetary ball mill Classic Line) at 200 rpm for 2 minutes, pass through a #200 mesh were performed to obtain a transition metal adsorbent 8 in which 0.0137 g/m$^2$ of a transition metal compound was adsorbed on the surface.
(Transition Metal Adsorbent 9)

A pot was put with 10 g of aluminosilicate glass particle (SiO$_2$: 32.2%, Al$_2$O$_3$: 19.3%, SrO: 26.9%, F: 8.7%, Na$_2$O: 4.0%, B$_2$O$_3$: 8.9%: manufactured by SHOFU INC, crushed product) having the average particle diameter of 0.5 μm, the pore volume of 0.11 cc/g and the specific surface area of 12.3 m$^2$/g, and 1 g of VOA, and was added with 200 g of alumina ball stone having φ2 mm. Then, after treating with a planetary mill (manufactured by Fritsch: P-5 planetary ball mill Classic Line) at 200 rpm for 2 minutes, pass through a #200 mesh were performed to obtain a transition metal adsorbent 9 in which 0.0081 g/m$^2$ of a transition metal compound was adsorbed on the surface.
(Transition Metal Adsorbent 10)

A pot was put with 10 g of porous silica zirconia particle (SiO$_2$: 92.1%, ZrO: 7.8%, others: 0.1%: manufactured by SHOFU INC.) having the average particle diameter of 3 μm, the pore volume of 0.21 cc/g and the specific surface area of 120 m$^2$/g, and 5 g of VOA, and was added with 200 g of alumina ball stone having φ2 mm. Then, after treating with a planetary mill (manufactured by Fritsch: P-5 planetary ball mill Classic Line) at 200 rpm for 2 minutes, pass through a #200 mesh were performed to obtain a transition metal adsorbent 10 in which 0.00417 g/m$^2$ of a transition metal compound was adsorbed on the surface.
(Transition Metal Adsorbent 11)

An eggplant flask putting was put with 10 g of barium sulfate (BMH-10: manufactured by Sakai Chemical Industry Co., Ltd.) having the average particle diameter of 12.0 μm, the pore volume of 0.04 cc/g and the specific surface area of 2.2 m$^2$/g, and 2 g of VOS to add the barium sulfate and the VOS into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 11 in which 0.09091 g/m$^2$ of a transition metal compound was adsorbed on the surface.
(Transition Metal Adsorbent 12)

An eggplant flask putting was put with 20 g of barium sulfate (BF-40: manufactured by Sakai Chemical Industry Co., Ltd.) having the average particle diameter of 0.015 μm, the pore volume of 0.09 cc/g and the specific surface area of 90 m$^2$/g, and 1 g of VOA to add the barium sulfate and the VOA into 20 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 12 in which 0.00056 g/m$^2$ of a transition metal compound was adsorbed on the surface.
(Transition Metal Adsorbent 13)

An eggplant flask putting was put with 10 g of PMMA particle (MB-8C: manufactured by Sekisui Plastics Co., Ltd.) having the average particle diameter of 8.3 μm, and the specific surface area of 4.3 m$^2$/g, and 1 g of VOS to add the PMMA and the VOS into 50 g of anhydrous ethanol and dispersion was performed in an ultrasonic washer for 10 minutes. Then, after removing ethanol under reduced pressure using an evaporator, vacuum drying was performed for 24 hours to obtain a transition metal adsorbent 13 in which 0.0233 g/m$^2$ of a transition metal compound was adsorbed on the surface.

(Transition Metal Adsorbent A)

A pot was put with 10 g of porous crosslinked PMMA particle (MBP-8: manufactured by Sekisui Plastics Co., Ltd.) having the average particle diameter of 8.1 μm, and the specific surface area of 86 m$^2$/g, and 2 g of VOA, and was added with 200 g of alumina ball stone having φ2 mm. Then, after treating with a planetary mill (manufactured by Fritsch: P-5 planetary ball mill Classic Line) at 200 rpm for 2 minutes, it was confirmed the prepared material taken out from the pot could not be used as an adsorbent because it was strongly aggregated and agglomerated.

[(b) Thiourea Derivative]
ATU: N-acetylthiourea
BTU: N-benzoylthiourea

[(c) Organic Peroxide Having a Hydroperoxide Group]
CHP: Cumene hydroperoxide
t-BHP: t-butyl hydroperoxide

[(d-1) Polymerizable Monomer Having No Acidic Group]
Bis-GMA: 2,2-bis [4-(3-methacryloyloxy)-2-hydroxypropoxyphenyl] propane
UDMA: 2,2,4-trimethyl hexamethylene bis (2-carbamoyloxyethyl) dimethacrylate
2.6E: 2,2-bis (4-methacryloyloxy polyethoxyphenyl) propane in which the average addition mole number of ethoxy groups is 2.6
TEGDMA: triethylene glycol dimethacrylate
NPG: neopentyl glycol dimethacrylate
2-HEMA: 2-hydroxyethyl methacrylate
CDMA: glycerol dimethacrylate

[(d-2) Polymerizable Monomer Having an Acidic Group]
MDP: 10-methacryloyloxydecyl dihydrogen phosphate
6-MHPA: (6-methacryloyloxy) hexylphosphonoacetate
4-MET: 4-methacryloyloxyethyl trimeritate

[Filler 1]

A silane coupling treatment solution prepared by stirring 10.0 g of water, 80.0 g of ethanol, 0.020 g of phosphoric acid, and 10.0 g of 3-methacryloyloxypropyl trimethoxysilane as a silane coupling agent at room temperature for 2 hours was added to 100.0 g of glass filler (GM344923: average particle diameter: 0.8 μm) manufactured by Schott and stirred for 30 minutes. Thereafter, a heat treatment was performed at 140° C. for 15 hours to obtain a filler 1.

[Filler 2]

A silane coupling treatment solution prepared by stirring 10.0 g of water, 80.0 g of ethanol, 0.020 g of phosphoric acid, and 5.0 g of 3-methacryloyloxypropyl trimethoxysilane as a silane coupling agent at room temperature for 2 hours was added to 100.0 g of spherical silica filler (SO—C2: average particle diameter: 0.5 μm) manufactured by Admatex and stirred for 30 minutes. Thereafter, a heat treatment was performed at 140° C. for 15 hours to obtain a filler 2.

[Other]
CQ: camphor quinone (photopolymerization initiator)
APO: 2,4,6-trimethylbenzoyl diphenylphosphine oxide (photopolymerization initiator)
BHT: 2,6-di-t-butyl-4-methylphenol (polymerization inhibitor)
EDTA: sodium ethylenediamine tetraacetate (metal supplementary material)
DMBE: ethyl 4-dimethylamino benzoate (polymerization accelerator)
VOA: vanadyl acetylacetonate (same material used for a transition metal adsorbent)

[Preparing Method of Paste]

For each of the first paste or the second paste shown in Tables 1 to 3, the (b) thiourea derivative, the (c) organic peroxide having a hydroperoxide group, the (d-1) acidic group-non-containing polymerizable monomer, the (d-2) acidic group-containing polymerizable monomer and others were added in a mixing container, and mixed by using a mix rotor VMRC-5 under the condition of 100 rpm for 24 hours to prepare a resin solution. Then, the filler and the (a) transition metal adsorbent in which a transition metal compound of the period 4 in the periodic table is adsorbed on an inorganic particle which is non-reactive with a transition metal of the period 4 in the periodic table were put into a kneading container, and kneaded by using a rotation and revolution mixer ARV-300 at 1400 rpm for 20 minutes to prepare a first paste and a second paste. Prepared first paste and second paste were filled into the double syringe of 5 mL manufactured by Mixpack (volume ratio of first paste to second paste is 1:1) so as to have a predetermined weight component ratio to prepare Compositions 1 to 31 as a two-paste type dental polymerizable composition.

[Measuring Method of Average Particle Diameter]

After ultrasonic wave was applied to the inorganic particles for 1 minute by using a particle size analyzer Microtrack MT3300EXII (manufactured by Nikkiso Co., Ltd.), the particle size was measured. Further, for samples having an average particle diameter of 200 nm or less, a picture of the inorganic particles was taken at an arbitrary magnification with a scanning electron microscope (Hitachi Science Systems Co., Ltd.: SEMEDX3 Type N), and the taken image was processed by using image analysis software, and a circle-equivalent diameter of 50 primary particles was measured, and then the average particle diameter was calculated based on the measured values.

[Measuring Method of Pore Volume and Specific Surface Area]

By using QUADRASORB evo (manufactured by Quantachrome Instruments), a specific surface area was measured by the BET multipoint method and a pore volume was measured by the BJH method. Note that before measuring, the inorganic particles were pretreated (heating at 200° C. under vacuum degassing for 2 hours) and adsorbed water was removed.

TABLE 1

| | | | (a) Kind of adosrbent | A-mount | (b) ATU | (b) BTU | (c) CHP | (c) t-BHP | (d-1) Bis-GMA | (d-1) UDMA | (d-1) 2.6E | (d-1) TEGDMA | (d-1) NPG | (d-1) 2-HEMA | (d-1) GDMA |
|---|---|---|---|---|---|---|---|---|---|---|---|---|---|---|---|
| Composition 1 | Example 1 | First | Adsorbent 1 | 1.0 | 2.0 | | | | 30.0 | 20.0 | | 10.0 | | | 20.0 |
| | | Second | | | | | | 1.5 | 30.0 | 20.0 | | 30.0 | | | 20.0 |

TABLE 1-continued

| | | | | | | | | | | | |
|---|---|---|---|---|---|---|---|---|---|---|---|
| Composition 2 | Example 2 | First Second | Adsorbent 2 | 0.7 | 2.2 1.0 | | 30.0 30.0 | 20.0 20.0 | 10.0 30.0 | | 20.0 20.0 |
| Composition 3 | Example 3 | First Second | Adsorbent 3 | 0.1 | 5.0 5.0 | | | 50.0 50.0 | 20.0 20.0 | | 10.0 30.0 |
| Composition 4 | Example 4 | First Second | Adsorbent 4 | 1.5 | 1.0 3.0 | | | 50.0 50.0 | 10.0 20.0 | | 10.0 30.0 |
| Composition 5 | Example 5 | First Second | Adsorbent 5 | 0.3 | 3.0 1.5 | | | 50.0 50.0 | 20.0 20.0 | | 10.0 30.0 |
| Composition 6 | Example 6 | First Second | Adsorbent 6 | 2.5 | 1.0 1.5 | | 30.0 30.0 | 20.0 20.0 | 20.0 30.0 | | 20.0 20.0 |
| Composition 7 | Example 7 | First Second | Adsorbent 7 | 1.2 | 1.5 2.0 | 2.0 | 30.0 30.0 | 20.0 20.0 | 20.0 30.0 | | 20.0 20.0 |
| Composition 8 | Example 8 | First Second | Adsorbent 5 | 5.0 | 0.8 0.6 | | 30.0 30.0 | 20.0 20.0 | 20.0 30.0 | | 20.0 20.0 |
| Composition 9 | Example 9 | First Adsorbent 1 Adsorbent 4 Second | | 1.0 1.0 | 2.0 1.5 | | 30.0 30.0 | 20.0 20.0 | 20.0 30.0 | | 20.0 20.0 |
| Composition 10 | Example 10 | First Second | Adsorbent 2 | 3.0 | 2.0 4.0 | 2.0 | 30.0 30.0 | 20.0 20.0 | 20.0 30.0 | | 20.0 20.0 |
| Composition 11 | Example 11 | First Second | Adsorbent 1 | 1.0 | 1.5 1.5 | | 20.0 20.0 | 30.0 30.0 | 30.0 30.0 | 10.0 10.0 | 10.0 10.0 |
| Composition 12 | Example 12 | First Second | Adsorbent 4 | 3.0 | 1.5 1.5 | | 20.0 20.0 | 30.0 30.0 | 10.0 30.0 | 10.0 10.0 | 10.0 10.0 |
| Composition 13 | Example 13 | First Second | Adsorbent 5 | 3.0 | 1.5 1.5 | | 20.0 20.0 | 30.0 30.0 | 10.0 30.0 | 10.0 10.0 | 10.0 10.0 |
| Composition 14 | Example 14 | First Second | Adsorbent 7 | 4.0 | 1.0 3.0 | | | 50.0 50.0 | 20.0 20.0 | | 10.0 30.0 |
| Composition 15 | Example 15 | First Second | Adsorbent 8 | 2.2 | 2.0 1.5 | | 30.0 30.0 | 20.0 20.0 | 10.0 30.0 | | 20.0 20.0 |
| Composition 16 | Example 16 | First Second | Adsorbent 9 | 1.5 | 2.0 1.5 | | 30.0 30.0 | 20.0 20.0 | 10.0 30.0 | | 20.0 20.0 |

| | | | (d-2) | | Filler | | Others | | | | | | Transition metal compound of the Period 4 in the periodic table based on 100 parts by weight of polymerizable monomer |
|---|---|---|---|---|---|---|---|---|---|---|---|---|---|
| | | | MDP | 6-MHPA | 4-MET | Filler 1 | Filler 2 | CQ | APO | BHT | EDTA | DMBE | VOA | |
| Composition 1 | Example 1 | First Second | 20.0 | | | 200.0 200.0 | | 0.5 | | | 0.1 | 0.3 | | 0.0455 |
| Composition 2 | Example 2 | First Second | 20.0 | | | 200.0 200.0 | | 0.8 | | | 0.1 | 0.6 | | 0.0318 |
| Composition 3 | Example 3 | First Second | | 15.0 | 5.0 | 300.0 300.0 | | 0.5 | | | 0.1 | 0.3 | | 0.0045 |
| Composition 4 | Example 4 | First Second | | 25.0 | 5.0 | 300.0 300.0 | | 2.0 | | | 0.1 | 0.3 | | 0.0682 |

TABLE 1-continued

| | | | | | | | | | | | | | | |
|---|---|---|---|---|---|---|---|---|---|---|---|---|---|---|
| Composition 5 | Example 5 | First | 15.0 | 5.0 | | 300.0 | 0.5 | 1.0 | | | | | | 0.0250 |
| | | Second | | | 300.0 | | | | 0.1 | | 0.3 | | | |
| Composition 6 | Example 6 | First | 10.0 | | | 200.0 | 0.5 | | | | | | | 0.0245 |
| | | Second | | | 200.0 | | | | 0.1 | | 0.3 | | | |
| Composition 7 | Example 7 | First | 10.0 | | | 200.0 | 0.5 | | | | | | | 0.0545 |
| | | Second | | | 200.0 | | | | 0.1 | | 0.3 | | | |
| Composition 8 | Example 8 | First | 10.0 | | | 200.0 | 0.5 | | | | | | | 0.4167 |
| | | Second | | | 200.0 | | | | 0.1 | | 0.3 | | | |
| Composition 9 | Example 9 | First | 10.0 | | | 200.0 | 0.5 | | | | | | | 0.0909 |
| | | Second | | | 200.0 | | | | 0.1 | | 0.3 | | | |
| Composition 10 | Example 10 | First | 10.0 | | | 200.0 | 0.5 | | | | | | | 0.1364 |
| | | Second | | | 200.0 | | | | 0.1 | | 0.3 | | | |
| Composition 11 | Example 11 | First | | | | 200.0 | 0.5 | | | | | | | 0.0455 |
| | | Second | | | 200.0 | | | | | 0.01 | 0.3 | | | |
| Composition 12 | Example 12 | First | 10.0 | | | 200.0 | 0.5 | | | | | | | 0.1364 |
| | | Second | | | 200.0 | | | | | 0.01 | 0.3 | | | |
| Composition 13 | Example 13 | First | 10.0 | | | 200.0 | 0.5 | | | | | | | 0.2500 |
| | | Second | | | 200.0 | | | | | 0.01 | 0.3 | | | |
| Composition 14 | Example 14 | First | | 15.0 | 5.0 | 200.0 | 0.5 | | | | | | | 0.1818 |
| | | Second | | | 200.0 | | | | 0.1 | | 0.3 | | | |
| Composition 15 | Example 15 | First | 10.0 | | | 200.0 | 0.5 | | | | | | | 0.1833 |
| | | Second | | | 200.0 | | | | 0.1 | | 0.3 | | | |
| Composition 16 | Example 16 | First | 10.0 | | | 200.0 | 0.5 | | | | | | | 0.0682 |
| | | Second | | | 200.0 | | | | 0.1 | | 0.3 | | | |

TABLE 2

| | | | (a) | | (b) | | (c) | | (d-1) | | | | | | |
|---|---|---|---|---|---|---|---|---|---|---|---|---|---|---|---|
| | | | Kind of adsorbent | Amount | ATU | BTU | CHP | BHP / t-BHP | Bis-GMA | UDMA | 2.6E | TEGDMA | NPG | 2-HEMA | GDMA |
| Composition 17 | Example 17 | First | Adsorbent 3 | 2.5 | 2.0 | | | | 30.0 | 20.0 | | 10.0 | | | 20.0 |
| | | | Adsorbent 8 | 0.5 | | | | | | | | | | | |
| | | Second | | | | | 1.5 | | 30.0 | 20.0 | | 30.0 | | | 20.0 |
| Composition 18 | Comparative Example 1 | First | | | 2.0 | | | | 30.0 | 20.0 | | 10.0 | | | 20.0 |
| | | Second | | | | | 1.5 | | 30.0 | 20.0 | | 30.0 | | | 20.0 |
| Composition 19 | Comparative Example 2 | First | Adsorbent 10 | 3.0 | 2.0 | | | | 30.0 | 20.0 | | 10.0 | | | 20.0 |
| | | Second | | | | | 1.5 | | 30.0 | 20.0 | | 30.0 | | | 20.0 |
| Composition 20 | Comparative Example 3 | First | Adsorbent 10 | 1.0 | 2.0 | | | | 30.0 | 20.0 | | 10.0 | | | 20.0 |
| | | Second | | | | | 1.5 | | 30.0 | 20.0 | | 30.0 | | | 20.0 |
| Composition 21 | Example 18 | First | Adsorbent 1 | 1.0 | 2.0 | | | | 30.0 | 20.0 | | 10.0 | | | 20.0 |
| | | Second | | | | | 10.0 | | 30.0 | 20.0 | | 30.0 | | | 20.0 |

TABLE 2-continued

| Composition | Example | First/Second | Adsorbent | | | | | | | | | | | |
|---|---|---|---|---|---|---|---|---|---|---|---|---|---|---|
| Composition 22 | Example 19 | First | Adsorbent 1 | 1.0 | 10.0 | | | 30.0 | 20.0 | | 10.0 | | | 20.0 |
| | | Second | | | | 1.5 | | 30.0 | 20.0 | | 30.0 | | | 20.0 |
| Composition 23 | Comparative Example 4 | First | | | 3.5 | | | 30.0 | 20.0 | | 10.0 | | | 20.0 |
| | | Second | | | | 1.5 | | 30.0 | 20.0 | | 30.0 | | | 20.0 |
| Composition 24 | Comparative Example 5 | First | | | 3.5 | | | 30.0 | 20.0 | | 10.0 | | | 20.0 |
| | | Second | | | | 1.5 | | 30.0 | 20.0 | | 30.0 | | | 20.0 |
| Composition 25 | Example 20 | First | Adsorbent 5 | 15.0 | | 1.5 | | 20.0 | 30.0 | | 10.0 | 10.0 | 10.0 | |
| | | Second | | | | | 1.5 | 20.0 | 30.0 | | 30.0 | 10.0 | 10.0 | |
| Composition 26 | Example 21 | First | Adsorbent 6 | 0.1 | | 1.0 | | 30.0 | 20.0 | | 20.0 | | | 20.0 |
| | | Second | | | | | 1.5 | 30.0 | 20.0 | | 30.0 | | | 20.0 |
| Composition 27 | Example 22 | First | Adsorbent 11 | 1.0 | | 2.0 | | 30.0 | 20.0 | | 10.0 | | | 20.0 |
| | | Second | | | | | 1.5 | 30.0 | 20.0 | | 30.0 | | | 20.0 |
| Composition 28 | Example 23 | First | Adsorbent 12 | 3.0 | | 2.0 | | 30.0 | 20.0 | | 10.0 | | | 20.0 |
| | | Second | | | | | 1.5 | 30.0 | 20.0 | | 30.0 | | | 20.0 |
| Composition 29 | Example 24 | First | Adsorbent 11 | 10.0 | | 2.0 | | 30.0 | 20.0 | | 10.0 | | | 20.0 |
| | | Second | | | | | 1.5 | 30.0 | 20.0 | | 30.0 | | | 20.0 |
| Composition 30 | Example 25 | First | Adsorbent 9 | 1.5 | | | 1.5 | 30.0 | 20.0 | | 10.0 | | | 20.0 |
| | | Second | | | | 2.0 | | 30.0 | 20.0 | | 30.0 | | | 20.0 |
| Composition 31 | Comparative Example 6 | First | Adsorbent 13 | 1.0 | | 2.0 | | 30.0 | 20.0 | | | | | 20.0 |
| | | Second | | | | | 1.5 | 30.0 | 20.0 | | 30.0 | | | 20.0 |
| Composition 32 | Example 26 | First | Adsorbent 5 | 20.0 | | 1.5 | | 20.0 | 30.0 | | 10.0 | 10.0 | 10.0 | |
| | | Second | | | | | 1.5 | 20.0 | 30.0 | | 30.0 | 10.0 | 10.0 | |

| | | | (d-2) | | | Filler | | | | Others | | | | Transition metal compound of the Period 4 in the periodic table based on 100 parts by weight of polymerizable monomer |
|---|---|---|---|---|---|---|---|---|---|---|---|---|---|---|
| | | | MDP | 6-MHPA | 4-MET | Filler 1 | Filler 2 | CQ | APO | BHT | EDTA | DMBE | VOA | |
| Composition 17 | Example 17 | First | 20.0 | | | | 200.0 | 0.5 | | | | | | 0.1553 |
| | | Second | | | | 200.0 | | | | 0.1 | | 0.3 | | |
| Composition 18 | Comparative Example 1 | First | 20.0 | | | | 200.0 | 0.5 | | | | | | 0.0000 |
| | | Second | | | | 200.0 | | | | 0.1 | | 0.3 | | |
| Composition 19 | Comparative Example 2 | First | 20.0 | | | | 200.0 | 0.5 | | | | | | 0.5000 |
| | | Second | | | | 200.0 | | | | 0.1 | | 0.3 | | |

TABLE 2-continued

| | | | | | | | | | | | |
|---|---|---|---|---|---|---|---|---|---|---|---|
| Composition 20 | Comparative Example 3 | First Second | 20.0 | 200.0 | 200.0 | 0.5 | 0.1 | 0.3 | | 0.1667 |
| Composition 21 | Example 18 | First Second | 20.0 | 200.0 | 200.0 | 0.5 | 0.1 | 0.3 | | 0.0455 |
| Composition 22 | Example 19 | First Second | 20.0 | 200.0 | 200.0 | 0.5 | 0.1 | 0.3 | | 0.0455 |
| Composition 23 | Comparative Example 4 | First Second | 20.0 | 200.0 | 200.0 | 0.5 | 0.1 | 0.3 | 0.09 | 0.0450 |
| Composition 24 | Comparative Example 5 | First Second | 20.0 | 200.0 | 200.0 | 0.5 | 0.1 | 0.3 | 0.8 | 0.4000 |
| Composition 25 | Example 20 | First Second | 20.0 | 200.0 | 200.0 | 0.5 | 0.01 | 0.3 | | 1.2500 |
| Composition 26 | Example 21 | First Second | 10.0 | 200.0 | 200.0 | 0.5 | 0.1 | 0.3 | | 0.0010 |
| Composition 27 | Example 22 | First Second | 20.0 | 200.0 | 200.0 | 0.5 | 0.1 | 0.3 | | 0.0833 |
| Composition 28 | Example 23 | First Second | 20.0 | 200.0 | 200.0 | 0.5 | 0.1 | 0.3 | | 0.0714 |
| Composition 29 | Example 24 | First Second | 20.0 | 200.0 | 200.0 | 0.5 | 0.1 | 0.3 | | 0.8333 |
| Composition 30 | Example 25 | First Second | 20.0 | 200.0 | 200.0 | 0.5 | 0.1 | 0.3 | | 0.0682 |
| Composition 31 | Comparative Example 6 | First Second | 20.0 | 200.0 | 200.0 | 0.5 | 0.1 | 0.3 | | 0.0455 |
| Composition 32 | Example 26 | First Second | 20.0 | 200.0 | 200.0 | 0.5 | 0.01 | 0.3 | | 1.2500 |

TABLE 3

| | | | (a) Kind of adsorbent | Amount | (b) | | (c) | | (d-1) | | | | | | |
|---|---|---|---|---|---|---|---|---|---|---|---|---|---|---|---|
| | | | | | ATU | BTU | CHP | t-BHP | Bis-GMA | UDMA | 2.6E | TEGDMA | NPG | 2-HEMA | GDMA |
| Composition 33 | Example 27 | First Second | Adsorbent 4 | 1.5 | 0.2 | | 3.0 | | | 50.0 50.0 | | 10.0 20.0 | | | 10.0 30.0 |
| Composition 34 | Example 28 | First Second | Adsorbent 4 | 1.5 | 0.1 | | 3.0 | | | 50.0 50.0 | | 10.0 20.0 | | | 10.0 30.0 |
| Composition 35 | Example 29 | First Second | Adsorbent 2 | 3.0 | 4.0 | 4.0 | 2.0 | | 30.0 30.0 | 20.0 20.0 | | 20.0 30.0 | | | 20.0 20.0 |
| Composition 36 | Example 30 | First Second | Adsorbent 2 | 3.0 | 5.0 | 5.0 | 2.0 | | 30.0 30.0 | 20.0 20.0 | | 20.0 30.0 | | | 20.0 20.0 |

TABLE 3-continued

| | | | | | | | | | | | | | |
|---|---|---|---|---|---|---|---|---|---|---|---|---|---|
| Com-position 37 | Example 31 | First Second | Adsorbent 5 | 5.0 | 2.0 | | 0.2 | 30.0 30.0 | 20.0 20.0 | | 20.0 30.0 | | 20.0 20.0 |
| Com-position 38 | Example 32 | First Second | Adsorbent 5 | 5.0 | 2.0 | | 0.1 | 30.0 30.0 | 20.0 20.0 | | 20.0 30.0 | | 20.0 20.0 |
| Com-position 39 | Example 33 | First Second | Adsorbent 2 | 3.0 | 2.0 | 2.0 | 6.0 | 30.0 30.0 | 20.0 20.0 | | 20.0 30.0 | | 20.0 20.0 |
| Com-position 40 | Example 34 | First Second | Adsorbent 6 | 2.5 | 1.0 | | 1.5 | 30.0 30.0 | 20.0 20.0 | | 28.0 30.0 | | 20.0 20.0 |
| Com-position 41 | Example 35 | First Second | Adsorbent 4 | 1.5 | 1.0 | | 3.0 | | 20.0 50.0 | | 20.0 | | 30.0 |
| Com-position 42 | Example 36 | First Second | Adsorbent 4 | 1.5 | 1.0 | | 3.0 | | 15.0 50.0 | | 20.0 | | 30.0 20.0 |
| Com-position 43 | Example 37 | First Second | Adsorbent 6 | 0.11 | 1.0 | | 1.5 | 30.0 30.0 | 20.0 20.0 | | 20.0 30.0 | | 20.0 |
| Com-position 44 | Example 38 | First Second | Adsorbent 5 | 24.0 | 1.5 | | 1.5 | 20.0 20.0 | 30.0 30.0 | 10.0 30.0 | 10.0 10.0 | 10.0 10.0 | |
| Com-position 45 | Example 39 | First Second | Adsorbent 4 | 1.5 | 1.0 | | 3.0 | 50.0 50.0 | 10.0 20.0 | | | | 10.0 30.0 |
| Com-position 46 | Example 40 | First Second | Adsorbent 1 | 1.0 | 2.0 | | 1.5 | 30.0 30.0 | 20.0 20.0 | | 10.0 30.0 | | 20.0 20.0 |
| Com-position 47 | Comparative Example 7 | First Second | Adsorbent 2 | 0.7 | | | 1.0 | 30.0 30.0 | 20.0 20.0 | | 10.0 30.0 | | 20.0 20.0 |
| Com-position 48 | Comparative Example 8 | First Second | Adsorbent 2 | 0.7 | | 2.2 | | 30.0 30.0 | 20.0 20.0 | | 10.0 30.0 | | 20.0 20.0 |

| | | | (d-2) | | | Filler | | Others | | | | | | Transition metal compound of the Period 4 in the periodic table based on 100 parts by weight of polymerizable monomer |
|---|---|---|---|---|---|---|---|---|---|---|---|---|---|---|
| | | | MDP | 6-MHPA | 4-MET | Filler 1 | Filler 2 | CQ | APO | BHT | EDTA | DMBE | VOA | |
| Composition 33 | Example 27 | First Second | | 25.0 | 5.0 | 300.0 | 300.0 | 2.0 | | 0.1 | | 0.3 | | 0.0682 |
| Composition 34 | Example 28 | First Second | | 25.0 | 5.0 | 300.0 | 300.0 | 2.0 | | 0.1 | | 0.3 | | 0.0682 |
| Composition 35 | Example 29 | First Second | 10.0 | | | 200.0 | 200.0 | 0.5 | | 0.1 | | 0.3 | | 0.1364 |
| Composition 36 | Example 30 | First Second | 10.0 | | | 200.0 | 200.0 | 0.5 | | 0.1 | | 0.3 | | 0.1364 |
| Composition 37 | Example 31 | First Second | 10.0 | | | 200.0 | 200.0 | 0.5 | | 0.1 | | 0.3 | | 0.4167 |
| Composition 38 | Example 32 | First Second | 10.0 | | | 200.0 | 200.0 | 0.5 | | 0.1 | | 0.3 | | 0.4167 |

TABLE 3-continued

| Composition 39 | Example 33 | First<br>Second | 10.0 | | | 200.0<br>200.0 | 0.5 | | 0.1 | | 0.3 | 0.1364 |
|---|---|---|---|---|---|---|---|---|---|---|---|---|
| Composition 40 | Example 34 | First<br>Second | 2.0 | | | 200.0<br>200.0 | 0.5 | | 0.1 | | 0.3 | 0.0245 |
| Composition 41 | Example 35 | First<br>Second | | 65.0 | 15.0 | 300.0<br>300.0 | | 2.0 | 0.1 | | 0.3 | 0.0682 |
| Composition 42 | Example 36 | First<br>Second | | 70.0<br>10.0 | 15.0 | 300.0<br>300.0<br>200.0 | 0.5 | 2.0 | 0.1 | | 0.3 | 0.0682 |
| Composition 43 | Example 37 | First<br>Second | | | | 200.0 | | | 0.1 | | 0.3 | 0.0010 |
| Composition 44 | Example 38 | First<br>Second | 20.0 | | | 200.0<br>200.0 | 0.5 | | | 0.01 | 0.3 | 1.2500 |
| Composition 45 | Example 39 | First<br>Second | | 25.0 | 5.0 | 300.0<br>300.0 | | 2.0 | 0.1 | | 0.3 | 0.0682 |
| Composition 46 | Example 40 | First<br>Second | 20.0 | | | | | | | | | 0.0455 |
| Composition 47 | Comparative Example 7 | First<br>Second | 20.0 | | | 200.0<br>200.0 | 0.8 | | 0.1 | | 0.6 | 1.2500 |
| Composition 48 | Comparative Example 8 | First<br>Second | 20.0 | | | 200.0<br>200.0 | 0.8 | | 0.1 | | 0.6 | 1.2500 |

The test method of each characteristic evaluated in the example and the comparative example is as follows. Each test was carried out under the conditions of automatic mixing with the mixing tip attached.

[Curing Time Measurement]

Curing time of the kneaded material of the pastes A and B was measured according to ISO 4049: 2009. Specifically, 0.8 g of the kneaded paste was filled in a container (4 mmφ×6 mm: manufactured by Teflon) attached with a thermocouple, and an exothermic curve due to a curing reaction was recorded. The time from the start of kneading of the paste to the peak of the exothermic curve was taken as the curing time, and the three measurements were averaged.

[Stability of Curability]

The above described curing time immediately after preparation of the paste was compared with that after storage at 40° C. for 5 months. The rating criteria were as follow:

S: The change rate was less than ±20%.
A: The change rate was 20% or more and less than 40%, or −20% or less and more than −40%.
B: The change rate was 40% or more and less than 60% or −40% or less and more than −60%.
C: Gelled or uncured Change rate (%)=[(Curing time after storage at 40° C. for 5 months)/(Curing time immediately after preparation)−1]×100

[Paste Stability]
<Color Difference>

The paste was discharged from the syringe, and the color tone (CIE L*a*b*) of the paste compounded with the transition metal compound was measured for immediately after preparation and after storage at 40° C. for 5 months, and then the color difference ΔE was calculated. The rating criteria were as follow:

S: ΔE was 0 or more and less than 2.
A: ΔE was 2 or more and less than 4.
B: ΔE was 4 or more and less than 8.
C: ΔE was 8 or more.

As the specific color measurement method, the paste was sampled in a mold with a thickness of 1.0 mm and an inner diameter of 15 mm, both ends were fixed with a thin glass plate with a thickness of 0.15±0.02 mm, and color measurement in a state of the thickness of 1.0 mm was performed under the conditions of SCE and a white background by using a colorimeter (CM-26d: manufactured by Konica Minolta).

<Characteristics>

Equal amounts of the first and the second pastes were discharged from the syringe, the feeling of kneading was confirmed by using a spatula. The rating criteria were as follow:

A: There was no change between the pastes immediately after preparation and after storage at 40° C. for 5 months.
B: There was slightly hardening between the pastes immediately after preparation and after storage at 40° C. for 5 months.
C: The change that makes clearly difficult to use such as gelation was observed.

The above tests were performed for compositions 1 to 48, and Table 4 shows the results. Compositions 1 to 17, 21, 22, 25 to 30, and 32 to 46 that satisfied storage stability and color stability are respectively described as Examples 1 to 40.

TABLE 4

| | | Curing time | | | | Paste stability | | |
|---|---|---|---|---|---|---|---|---|
| | | immediately after preparation | 40° C. for 5 months | Change rate | | Color difference | | Characteristics |
| Example 1 | Composition 1 | 205 | 220 | 7.3 | S | 0.6 | S | A |
| Example 2 | Composition 2 | 457 | 500 | 9.4 | S | 1.2 | S | A |
| Example 3 | Composition 3 | 316 | 308 | −2.5 | S | 1.1 | S | A |
| Example 4 | Composition 4 | 188 | 176 | −6.4 | S | 1.8 | S | A |
| Example 5 | Composition 5 | 284 | 303 | 6.7 | S | 0.7 | S | A |
| Example 6 | Composition 6 | 240 | 249 | 3.8 | S | 0.5 | S | A |
| Example 7 | Composition 7 | 172 | 221 | 28.5 | A | 1.4 | S | A |
| Example 8 | Composition 8 | 328 | 374 | 14.0 | S | 0.5 | S | A |
| Example 9 | Composition 9 | 228 | 230 | 0.9 | S | 1.2 | S | A |
| Example 10 | Composition 10 | 152 | 143 | −5.9 | S | 1.1 | S | A |
| Example 11 | Composition 11 | 309 | 377 | 22.0 | A | 1.5 | S | A |
| Example 12 | Composition 12 | 245 | 257 | 4.9 | S | 0.5 | S | A |
| Example 13 | Composition 13 | 194 | 209 | 7.7 | S | 0.2 | S | A |
| Example 14 | Composition 14 | 195 | 254 | 30.3 | A | 1.4 | S | A |
| Example 15 | Composition 15 | 242 | 304 | 25.6 | A | 1.4 | S | A |
| Example 16 | Composition 16 | 325 | 408 | 25.5 | A | 3.2 | A | A |
| Example 17 | Composition 17 | 216 | 211 | −2.3 | S | 1.1 | S | A |
| Comparative Example 1 | Composition 18 | 820 | Uncured | — | C | 0.5 | S | C: Uncured |
| Comparative Example 2 | Composition 19 | 247 | 302 | 22.3 | A | 9.2 | C | A |
| Comparative Example 3 | Composition 20 | 503 | 554 | 10.1 | S | 8.3 | C | A |
| Example 18 | Composition 21 | 184 | 92 | −50.0 | B | 3.2 | A | B |
| Example 19 | Composition 22 | 209 | 83 | −60.3 | B | 2.9 | A | B |
| Comparative Example 4 | Composition 23 | 642 | Uncured | — | C | 10.3 | C | C: Uncured |
| Comparative Example 5 | Composition 24 | 258 | Gelation | — | C | — | — | C: Uncured |
| Example 20 | Composition 25 | 120 | 78 | −35.0 | A | 4.5 | B | B |
| Example 21 | Composition 26 | 700 | 932 | 33.1 | A | 0.4 | S | A |
| Example 22 | Composition 27 | 325 | 224 | −31.1 | A | 5.2 | B | B |
| Example 23 | Composition 28 | 351 | 478 | 36.2 | A | 0.4 | S | A |
| Example 24 | Composition 29 | 214 | 145 | −32.2 | A | 6.1 | B | B |
| Example 25 | Composition 30 | 331 | 209 | −36.9 | A | 3.2 | A | B |
| Comparative Example 6 | Composition 31 | 265 | Gelation | — | C | — | — | C: Uncured |
| Example 26 | Composition 32 | 90 | 85 | −5.6 | S | 5.5 | B | B |
| Example 27 | Composition 33 | 405 | 407 | 0.5 | S | 1.2 | S | A |
| Example 28 | Composition 34 | 555 | 547 | −1.4 | S | 3.1 | A | A |
| Example 29 | Composition 35 | 241 | 240 | −0.4 | S | 1.1 | S | A |
| Example 30 | Composition 36 | 306 | 255 | −16.7 | S | 3.2 | A | A |
| Example 31 | Composition 37 | 505 | 545 | 7.9 | S | 2.9 | S | A |
| Example 32 | Composition 38 | 610 | 708 | 16.1 | S | 3.5 | A | A |
| Example 33 | Composition 39 | 100 | 95 | −5.0 | S | 2.5 | S | A |
| Example 34 | Composition 40 | 251 | 255 | 1.6 | S | 1.9 | S | A |
| Example 35 | Composition 41 | 208 | 201 | −3.4 | S | 1.8 | S | A |
| Example 36 | Composition 42 | 386 | 411 | 6.5 | S | 3.1 | A | A |
| Example 37 | Composition 43 | 677 | 822 | 21.4 | A | 4 | B | A |
| Example 38 | Composition 44 | 82 | 103 | 25.6 | A | 4.8 | B | B |
| Example 39 | Composition 45 | 270 | 289 | 7.0 | S | 1.5 | S | A |
| Example 40 | Composition 46 | 454 | 474 | 4.4 | S | 4.2 | B | B |
| Comparative Example 7 | Composition 47 | Uncured | — | — | — | — | — | — |
| Comparative Example 8 | Composition 48 | Uncured | — | — | — | — | — | — |

In Examples 1 to 40 in which each component satisfies the constitution of the present disclosure, even after storage at 40° C. for 5 months, the composition was cured, no significant color change was observed, and it could withstand the use for a dental composition applied to the oral cavity, and therefore high storage stability was exhibited. Further, in Examples 7, 11, 14 to 16, 18 to 25, 37, 38, it was confirmed that although the curing time after storage at 40° C. for 5 months was shortened or delayed, it was not a significant change in operation.

For Example 11, although the reason was unknown, it was considered that the polymerization accelerating effect was lowered by not containing the (d-2) acidic group-containing polymerizable monomer.

For Examples 7, 14, 15 and 16, it was considered that the reactivity of the transition metal compound adsorbed on the spherical silica or the fluoroaluminosilicate glass lowered for some reason.

In Examples 18 and 19, the curing time was shortened after storage at 40° C. for 5 months. It was considered that these were caused by an excessive compounding amount of the (b) thiourea derivative or the (c) organic peroxide having a hydroperoxide group.

For Examples 20 and 38, it was considered that shortening or delay in curing occurred because a content of a transition metal compound was slightly excess with respect to the (b) thiourea derivative and the (c) organic peroxide having a hydroperoxide group.

In Examples 22, 24 and 26, it was considered that a slight discoloration was caused since the adsorption amount of transition metal was slightly large and the transition metal compound was localized in the composition.

In Examples 21, 23, 37, a slight delay was observed in the curing time after storage at 40° C. for 5 months. It is considered in Example 21 that the reason is that the transition metal compound was too little with respect to the (b) thiourea derivative and the (c) organic peroxide having a hydroperoxide group, and in Example 20 that the adsorption amount of transition metal of the transition metal adsorbent was too little.

In the composition of Example 25, the respective pastes in which the (b) thiourea derivative and the (c) organic peroxide having a hydroperoxide group were contained in Example 16 were replaced from each other, and a shortening of the curing time within an allowable range was observed. It was considered that the activity was unintentionally increased by compounding the (c) organic peroxide having a hydroperoxide group and the transition metal compound in the same paste for a long time.

For Example 28, it was considered that slight discoloration occurred since the content of the (b) thiourea derivative was slightly little.

For Example 30, it was considered that slight discoloration occurred since the content of the (b) thiourea derivative was slightly large.

For Example 32, it was considered that slight discoloration occurred since the content of the (c) organic peroxide having a hydroperoxide group was slightly little.

For Example 36, it was considered that slight discoloration occurred since the content of the (d-2) acidic group-containing polymerizable monomer was slightly large.

For Example 40, it was considered that slight discoloration occurred and paste properties were lowered since the components other than (a) to (d) are not contained.

The curing time of these dental compositions can be arbitrarily adjusted by adding a plurality of polymerization accelerators, increasing or decreasing the compounding amount of the polymerization accelerator and increasing or decreasing the adsorption amount of the transition metal compound. Furthermore, since it is possible to adjust physical characteristics such as bending strength, flexural modulus and film thickness by appropriately changing the compounding amount and the particle diameter of the filler and the like, it is preferable to use as a dental two-paste type polymerizable composition such as a dental cement, a dental adhesive material, a dental autopolymerizing resin and a dental abutment construction material.

Since Comparative Example 1 did not contain a transition metal compound, it was confirmed that the polymerization accelerating effect was not obtained, the curing time immediately after preparation was extremely long, and the curing did not occur after storage at 40° C. for 5 months.

In Comparative Examples 2 and 3, although no significant change was observed in the curing time, discoloration of the composition was observed after storage at 40° C. for 5 months. It was considered that the transition metal compound adsorbed in the pores remained for a long period of time to led discoloration.

In comparative Example 4, discoloration was observed after storage at 40° C. for 5 months, and in Comparative Example 5, gelation was observed after storage at 40° C. for 5 months. It was considered that the reason is that since the transition metal compound was not adsorbed on inorganic particles or the like and dispersed in the paste, the transition metal compound was microscopically localized to led discoloration or gelation. Further, although the compounding amount of the transition metal compound of Comparative Example 4 was almost the same as that of Example 1, the curing time was long in Comparative Example 4, therefore it could be considered that the dispersion in the composition was insufficient.

In Comparative Example 6, although the curing time immediately after preparation was appropriate, it was confirmed that the first paste was gelled after storage at 40° C. for 5 months. Although the compounding amount of the transition metal compound was the same as that in Example 1, it was considered that PMMA particles as the adsorbed particles were swelled or dissolved in the polymerizable monomer to release the dispersed state, and the transition metal compound was localized in the composition to induce gelation. In Comparative Example 7 and Comparative Example 8, curing was not achieved.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present disclosure is widely used in the dental field, as a dental resin cement, a dental abutment construction material, a dental adhesive material, a dental coating material, a pit and fissure plugging material, a composite resin, a dental autopolymerizing resin, a dental pretreatment material, a denture base material and the like, and therefore can be industrially applied.

What is claimed is:

1. A dental curable composition, containing
   (a) transition metal adsorbent in which a transition metal compound of the period 4 in the periodic table is adsorbed on an inorganic particle which is non-reactive with a transition metal of the period 4 in the periodic table,
   (b) thiourea derivative,
   (c) organic peroxide having a hydroperoxide group, and
   (d) polymerizable monomer, wherein
   the (d) polymerizable monomer contains (d-1) polymerizable monomer that does not contain an acidic group, and wherein
   a pore volume of the inorganic particle which is non-reactive with a transition metal of the period 4 in the periodic table is 0.2 cc/g or less.

2. The dental curable composition of claim 1, wherein the (d) polymerizable monomer further contains (d-2) acidic group-containing polymerizable monomer.

3. The dental curable composition of claim 2, wherein the dental curable composition contains 1 to 40 parts by weight of the (d-2) acidic group-containing polymerizable monomer based on 100 parts by weight of the (d) polymerizable monomer.

4. The dental curable composition of claim 1, wherein a first paste contains the (a) transition metal adsorbent in which a transition metal compound of the period 4 in the periodic table is adsorbed on an inorganic particle which is non-reactive with a transition metal of the period 4 in the periodic table, the (b) thiourea derivative and the (d) polymerizable monomer, and a second paste contains the (c) organic peroxide having a hydroperoxide group and the (d) polymerizable monomer.

5. The dental curable composition of claim 1, wherein
an amount of the transition metal compound of the 4th period adsorbed in the (a) transition metal adsorbent in which a transition metal compound of the period 4 in the periodic table is adsorbed on an inorganic particle which is non-reactive with a transition metal of the period 4 in the periodic table is 0.001 to 0.1 g/m².

6. The dental curable composition of claim 1, wherein
the dental curable composition contains, based on 100 parts by weight of the total amount of the polymerizable monomer,
0.05 to 7.5 parts by weight of the (a) transition metal adsorbent in which a transition metal compound of the period 4 in the periodic table is adsorbed on an inorganic particle which is non-reactive with a transition metal of the period 4 in the periodic table,
0.001 to 1 parts by weight of the transition metal compound contained in the (a) transition metal adsorbent in which a transition metal compound of the period 4 in the periodic table is adsorbed on an inorganic particle which is non-reactive with a transition metal of the period 4 in the periodic table,
0.1 to 4 parts by weight of the (b) thiourea derivative, and
0.1 to 3 parts by weight of the (c) organic peroxide having a hydroperoxide group.

7. The dental curable composition of claim 6, wherein
the dental curable composition further contains, based on 100 parts by weight of the total amount of the polymerizable monomer,
0.5 to 350 parts by weight of a filler,
0.01 to 5 parts by weight of a photopolymerization initiator, and
0.01 to 5 parts by weight of a polymerization accelerator.

8. The dental curable composition of claim 3, wherein
a first paste contains the (a) transition metal adsorbent in which a transition metal compound of the period 4 in the periodic table is adsorbed on an inorganic particle which is non-reactive with a transition metal of the period 4 in the periodic table, the (b) thiourea derivative and the (d) polymerizable monomer, and
a second paste contains the (c) organic peroxide having a hydroperoxide group and the (d) polymerizable monomer.

9. The dental curable composition of claim 8, wherein
an amount of the transition metal compound of the 4th period adsorbed in the (a) transition metal adsorbent in which a transition metal compound of the period 4 in the periodic table is adsorbed on an inorganic particle which is non-reactive with a transition metal of the period 4 in the periodic table is 0.001 to 0.1 g/m².

10. The dental curable composition of claim 9, wherein
the dental curable composition contains, based on 100 parts by weight of the total amount of the polymerizable monomer,
0.05 to 7.5 parts by weight of the (a) transition metal adsorbent in which a transition metal compound of the period 4 in the periodic table is adsorbed on an inorganic particle which is non-reactive with a transition metal of the period 4 in the periodic table,
0.001 to 1 parts by weight of the transition metal compound contained in the (a) transition metal adsorbent in which a transition metal compound of the period 4 in the periodic table is adsorbed on an inorganic particle which is non-reactive with a transition metal of the period 4 in the periodic table,
0.1 to 4 parts by weight of the (b) thiourea derivative, and
0.1 to 3 parts by weight of the (c) organic peroxide having a hydroperoxide group.

11. The dental curable composition of claim 10, wherein
the dental curable composition further contains, based on 100 parts by weight of the total amount of the polymerizable monomer,
0.5 to 350 parts by weight of a filler,
0.01 to 5 parts by weight of a photopolymerization initiator, and
0.01 to 5 parts by weight of a polymerization accelerator.

12. The dental curable composition of claim 4, wherein
an amount of the transition metal compound of the 4th period adsorbed in the (a) transition metal adsorbent in which a transition metal compound of the period 4 in the periodic table is adsorbed on an inorganic particle which is non-reactive with a transition metal of the period 4 in the periodic table is 0.001 to 0.1 g/m².

13. The dental curable composition of claim 12, wherein
the dental curable composition contains, based on 100 parts by weight of the total amount of the polymerizable monomer,
0.05 to 7.5 parts by weight of the (a) transition metal adsorbent in which a transition metal compound of the period 4 in the periodic table is adsorbed on an inorganic particle which is non-reactive with a transition metal of the period 4 in the periodic table,
0.001 to 1 parts by weight of the transition metal compound contained in the (a) transition metal adsorbent in which a transition metal compound of the period 4 in the periodic table is adsorbed on an inorganic particle which is non-reactive with a transition metal of the period 4 in the periodic table,
0.1 to 4 parts by weight of the (b) thiourea derivative, and
0.1 to 3 parts by weight of the (c) organic peroxide having a hydroperoxide group.

14. The dental curable composition of claim 13, wherein
the dental curable composition further contains, based on 100 parts by weight of the total amount of the polymerizable monomer,
0.5 to 350 parts by weight of a filler,
0.01 to 5 parts by weight of a photopolymerization initiator, and
0.01 to 5 parts by weight of a polymerization accelerator.

15. The dental curable composition of claim 5, wherein
the dental curable composition contains, based on 100 parts by weight of the total amount of the polymerizable monomer,
0.05 to 7.5 parts by weight of the (a) transition metal adsorbent in which a transition metal compound of the period 4 in the periodic table is adsorbed on an inorganic particle which is non-reactive with a transition metal of the period 4 in the periodic table,
0.001 to 1 parts by weight of the transition metal compound contained in the (a) transition metal adsorbent in which a transition metal compound of the period 4 in the periodic table is adsorbed on an inorganic particle which is non-reactive with a transition metal of the period 4 in the periodic table,
0.1 to 4 parts by weight of the (b) thiourea derivative, and
0.1 to 3 parts by weight of the (c) organic peroxide having a hydroperoxide group.

16. The dental curable composition of claim 15, wherein the dental curable composition further contains, based on
100 parts by weight of the total amount of the polymerizable monomer,
0.5 to 350 parts by weight of a filler,
0.01 to 5 parts by weight of a photopolymerization initiator, and
0.01 to 5 parts by weight of a polymerization accelerator.

* * * * *